United States Patent
Reyes et al.

(10) Patent No.: US 9,233,074 B2
(45) Date of Patent: Jan. 12, 2016

(54) DELAYED RELEASE FILM COATINGS CONTAINING CALCIUM SILICATE AND SUBSTRATES COATED THEREWITH

(71) Applicant: BPSI Holdings, LLC., Wilmington, DE (US)

(72) Inventors: George Reyes, Perkiomenville, PA (US); Charles R. Cunningham, Ambler, PA (US); Thomas P. Farrell, Warrington, PA (US); Cara Young, Blue Bell, PA (US)

(73) Assignee: BPSI HOLDINGS, LLC, Wilmington, DE (US)

( * ) Notice: Subject to any disclaimer, the term of this patent is extended or adjusted under 35 U.S.C. 154(b) by 0 days.

(21) Appl. No.: 14/189,508

(22) Filed: Feb. 25, 2014

(65) Prior Publication Data

US 2014/0248350 A1    Sep. 4, 2014

Related U.S. Application Data

(60) Provisional application No. 61/771,495, filed on Mar. 1, 2013.

(51) Int. Cl.
*A61K 9/28* (2006.01)

(52) U.S. Cl.
CPC ............. *A61K 9/2813* (2013.01); *A61K 9/2846* (2013.01); *A61K 9/2886* (2013.01)

(58) Field of Classification Search
CPC .. A61K 9/2813; A61K 9/2846; A61K 9/2886
See application file for complete search history.

(56) References Cited

U.S. PATENT DOCUMENTS

| | | | |
|---|---|---|---|
| 2,951,791 A | 9/1960 | Stearns | |
| 4,278,718 A | 7/1981 | Billings | |
| 5,035,899 A * | 7/1991 | Saeki et al. | 424/480 |
| 6,039,976 A * | 3/2000 | Mehra et al. | 424/480 |
| 6,551,617 B1 * | 4/2003 | Corbo et al. | 424/465 |
| 2001/0022972 A1 * | 9/2001 | Chittamuru et al. | 424/439 |
| 2003/0203019 A1 * | 10/2003 | Cornelius et al. | 424/465 |
| 2006/0078614 A1 | 4/2006 | Venkatesh | |
| 2009/0022795 A1 | 1/2009 | Ghosh et al. | |
| 2010/0291183 A1 * | 11/2010 | Farrell et al. | 424/443 |
| 2012/0058194 A1 | 3/2012 | Vaya et al. | |
| 2012/0141588 A1 * | 6/2012 | Chopra et al. | 424/489 |

FOREIGN PATENT DOCUMENTS

WO    2012028203    3/2012

OTHER PUBLICATIONS

Evonik Industries AG. EUDRAGIT(R) L 100 and EUDRAGIT(R) S 100, Dec. 2012, pp. 1-7.
Zaks, A., et al., The Effect of Water on Enzyme Action in Organic Media, The Journal of Biological Chemistry, vol. 263, No. 17, pp. 8017-8021, 1988.
Evonik Industries AG. EUDRAGIT(R) E 100, EUDRAGIT(R) E PO and EUDRAGIT(R) E 12,5. pp. 1-6, Dec. 2012.
Sinko, K., Influence of Chemical Conditions . . . , vol. 3, pp. 704-740, 2010.
International Search Report issued in PCT Application No. PCT/US14/18341.

* cited by examiner

*Primary Examiner* — Anoop Singh
*Assistant Examiner* — Doan Phan
(74) *Attorney, Agent, or Firm* — Lucas & Mercanti, LLP

(57) ABSTRACT

The present invention includes pH dependent, dry film coating compositions containing calcium silicate for use on orally-ingestible substrates such as tablets and the like. The film coating compositions can be applied as an aqueous suspension either directly to a substrate or after the substrate has been coated with a subcoat. In preferred aspects, the polymer is either an enteric or reverse-enteric polymer. Methods of preparing the dry film coatings, methods of preparing corresponding aqueous suspensions, methods of applying the coatings to substrates and the coated substrates themselves are also disclosed.

21 Claims, No Drawings

DELAYED RELEASE FILM COATINGS CONTAINING CALCIUM SILICATE AND SUBSTRATES COATED THEREWITH

CROSS-REFERENCE TO RELATED APPLICATIONS

This application claims the benefit of priority from U.S. Provisional Patent Application Ser. No. 61/771,495, filed Mar. 1, 2013, the contents of which are incorporated herein by reference.

FIELD OF THE INVENTION

This invention relates to the field of aqueous film coating dispersions for coating pharmaceutical tablets and the like for pH dependent release of the ingredients of coated tablets. It provides a non-toxic, edible, dry powder composition for use in making an aqueous coating dispersion that may be used in coating pharmaceuticals with a pH dependent coating. More specifically, the present invention relates to the use of calcium silicate as a reversible plasticizer sequestrant that enables the inventive compositions to remain free flowing without agglomeration in the dry state and to be dispersed in water and coated at relatively fast spray rates and relatively low weight gains while still maintaining pH dependent release properties. The invention also relates to pharmaceutical substrates having such film coatings and methods of preparing the same.

BACKGROUND OF THE INVENTION

WO2008/043701 discloses pharmaceutical solid dosage forms comprising a therapeutically effective compound (i.e. a drug) micro-embedded into an ionic water-insoluble polymer matrix. A preferred micro-embedding process involves depositing an ethanolic solution of a therapeutically effective compound and an ionic water-insoluble polymer on microcrystalline cellulose (MCC) spheres using a fluid bed coater. The disclosed water-insoluble polymers include those which are only soluble in water above pH 5.5. EUDRAGIT L100-55, a methacrylic acid copolymer, is listed as a suitable water-insoluble polymer that meets this definition. The MCC spheres, coated with the drug/ionic water-insoluble polymer, were further coated with a distinct, protective seal coat consisting of polyvinylpyrrolidone (PVP) and calcium silicate. PVP and calcium silicate were added in two separate steps to ethyl alcohol (200 proof) to form the seal coating suspension. A seal coat is used to protect the drug from direct exposure to ambient storage conditions. While the function of the calcium silicate is not discussed in WO2008/043701, it is noteworthy that the calcium silicate is part of a separate coating layer from the methacrylic acid copolymer with no plasticizer included. There is therefore no beneficial interaction between the methacrylic acid copolymer and calcium silicate.

U.S. Pat. No. 6,420,473 describes dry enteric film coating compositions comprising an acrylic resin, an alkalizing agent, a detackifier and, optionally, additional ingredients such as plasticizers, flow aids, pigments, surfactants, anti-agglomerating agents, secondary film formers and secondary detackifiers. Calcium silicate is not listed in the '473 patent, and the concept of a reversible plasticizer sequestrant was not disclosed therein.

While the formulations disclosed in U.S. Pat. No. 6,420,473 are commercially useful, there is still a need for improved pH dependent coatings that can be applied at lower coating weight gains than prior art coatings to shorten overall process times.

SUMMARY OF THE INVENTION

It has been surprisingly found that the inclusion of calcium silicate, which functions as a reversible plasticizer sequestrant, in pH dependent film coating compositions also reduces the tendency for agglomeration of the dry film coating composition. Aqueous film coating compositions containing a sufficient amount of calcium silicate allow for rapid tablet coating processes, and, in most aspects of the invention, maintain the delayed release properties of the pH dependent polymer at relatively low weight gains when compared to prior art compositions while still preserving enteric effects. The resulting coated substrates are also resistant to agglomeration even when stored at relatively high temperature and humidity.

In one aspect of the invention, there are provided dry powder film coating compositions for the pharmaceutical and related arts. The dry pH dependent film coating compositions include one or more pH dependent polymers, calcium silicate, and optionally one or more plasticizers, alkalizing agents, acidifying agents, detackifiers, pigments and surfactants.

In another aspect of the invention, there are provided aqueous dispersions of the film coating compositions described above. The dispersions preferably contain from about 10 to about 25% non-water ingredients content. Still further aspects include methods of coating orally-ingestible substrates with the coating suspensions as well as the coated substrates prepared by these methods.

DETAILED DESCRIPTION OF THE INVENTION

For purposes of the present invention, the following terms are given further clarification as to their meanings:

"orally-ingestible substrate" shall be understood to mean any pharmaceutically acceptable dosage form, e.g. tablet, capsule, caplet, drug-layered sugar spheres or similar beads, drug particles, etc. or any other veterinary or confectionary product capable of being taken via the oral route of administration;

"dry powder" shall be understood to mean powders which are relatively dry to the touch rather than powders which are essentially without moisture content; and "ambient temperature" shall be understood to mean temperatures generally in the range of from about 20° C. (68° F.) to about 30° C. (86° F.)+/−3° C.

"pH dependent" shall be understood to mean a polymer or coating that is soluble in one pH range but not in another. For example, a traditional "enteric" polymer or coating is insoluble at low pH, up to about 5 for example, but is soluble at higher pH i.e. about 6.5 or greater. Conversely, a "reverse-enteric polymer" or coating is soluble at low pH up to about pH 5 for example, but is insoluble at higher pH's i.e. about pH 6.5 or greater.

The dry pH dependent film coating compositions comprise one or more pH dependent polymers, calcium silicate, optionally one or more plasticizers, and, in most cases, one or more optional ingredients such as alkalizing agents, acidifying agents, detackifiers, pigments, surfactants and the like.

In some further embodiments, there are provided dry film coating compositions containing a pH-dependent polymer, an amount of a plasticizer sufficient for plasticizing the pH-dependent polymer and an amount of a calcium silicate sufficient to reversibly sequester the plasticizer from the pH-dependent polymer while in the dry state.

The pH dependent polymer may be any of the commonly used enteric or reverse-enteric polymers. Suitable pH dependent, enteric polymers include methacrylic acid copolymers, polyvinylacetate phthalate, hydroxypropylmethyl cellulose acetate succinate, hydroxypropylmethyl cellulose phthalate and cellulose acetate phthalate. Suitable methacrylic acid copolymers include: poly(methacrylic acid, methyl methacrylate) 1:1 sold, for example, under the Eudragit L100 trade name; poly(methacrylic acid, ethyl acrylate) 1:1 sold, for example, under the Eudragit L100-55 trade name; partially-neutralized poly(methacrylic acid, ethyl acrylate) 1:1 sold, for example, under the Kollicoat MAE-100P trade name; and poly(methacrylic acid, methyl methacrylate) 1:2 sold, for example, under the Eudragit S100 trade name.

Enteric polymers and coatings are useful in the pharmaceutical arts, because they prevent the release of active ingredients in the gastric juices of the stomach, where, in some cases, the active ingredients may quickly degrade.

Suitable pH dependent, reverse-enteric polymers include aminomethacrylate copolymers such as poly(butyl methacrylate, 2-dimethylaminoethyl methacrylate, methyl methacrylate) 1:2:1 sold, for example, under the Eudragit E PO trade name and similar polymers as described in PCT publications WO2012/116940 and WO2012/116941, the contents of each of which are incorporated herein by reference.

Reverse-enteric polymers and coatings are useful in the pharmaceutical arts, because they can prevent even small quantities of active ingredients from being released in the saliva and, hence, can serve as taste masking agents, especially when the taste of the active ingredient is bitter or otherwise objectionable.

In most embodiments, the total amount of pH dependent polymer included in the powder mixtures of the present invention is from about 20 to about 70% by weight. In some preferred embodiments, it ranges from about 25 to about 65% and more preferably ranges from about 30 to about 60% by weight of the dry coating composition.

In preferred aspects of the invention, calcium silicate functions as a reversible plasticizer sequestrant. While not wishing to be bound by any particular theory, it is believed that, owing to its high surface area, calcium silicate can absorb and sequester plasticizers such as triethyl citrate and poloxamers when it is formulated in a dry enteric film coating formulation and maintained in the dry state. Surprisingly and advantageously, the calcium silicate then releases the plasticizer when the film coating composition is dispersed in water, so that the plasticizer can beneficially interact with the pH dependent polymer and facilitate film formation on the substrate surface.

In some alternative embodiments wherein poly(butyl methacrylate, 2-dimethylaminoethyl methacrylate, methyl methacrylate) 1:2:1 is used as the pH dependent polymer, it has been surprisingly found that calcium silicate also prevents powder agglomeration even when a plasticizer is not included in the formulation.

Preferred grades of calcium silicate have a surface area of 50 $m^2$/gram or greater. More preferred grades of calcium silicate have a surface area of 120 $m^2$/gram or greater. The most preferred grades of calcium silicate have a surface area of 250 $m^2$/gram or greater.

In most embodiments, the amount of calcium silicate included in the dry film coating compositions is an amount which is sufficient to reversibly sequester a sufficient amount of the plasticizer from the pH-dependent polymer while in the dry form so that when an aqueous suspension of the film coating composition is made therefrom, the desired plasticizing effect is observable. Generally, the amount of calcium silicate included in the powder mixtures is from about 0.5-15%. In some preferred embodiments, the amount ranges from about 1 to about 10% and, more preferably, ranges from about 3 to about 9%. Alternatively, the calcium silicate comprises about 3-8% of the composition.

In those aspects of the invention where a plasticizer is included in the film coating compositions, the amount used is dependent at least in part upon the plasticizer selected, the type and amount of pH-dependent polymer included in the film coating composition. As will be appreciated by those of ordinary skill, the amount of plasticizer included is an amount which achieves sufficient plasticizing, i.e. improvement in the softening and/or lowering of the glass transition temperature, of the polymer when the film coating composition is in the form of an aqueous suspension. A non-limiting list of suitable plasticizers includes triethyl citrate, tributyl citrate, glyceryl triacetate, acetyltriethyl citrate, dibutyl sebacate, diethyl phthalate, polyethylene glycol having a molecular weight in the range of 200 to 8000, glycerol, castor oil, copolymers of propylene oxide and ethylene oxide, or mixtures thereof. Triethyl citrate and triblock copolymers of propylene oxide and ethylene oxide, generically referred to as poloxamers, are especially preferred plasticizers. Poloxamers are characterized by having a central polypropylene oxide) chain flanked on either side by poly(ethylene oxide) chains. Exemplary poloxamers are those sold under the KOLLIPHOR and PLURONIC trade names. In most embodiments, the amount of plasticizer is from about 5 to about 20% by weight of the pH dependent polymer content. In some preferred embodiments, it ranges from about 7 to about 18% and more preferably ranges from about 10 to about 15% by weight of the pH dependent polymer content.

For pH dependent polymers comprising carboxylic acid groups, suitable alkalizing agents (or neutralizing agents) include, for example, sodium bicarbonate, potassium bicarbonate and ammonium carbonate. Each of the foregoing as well as those known to those of ordinary skill not specifically mentioned herein, are useful in compositions that comprise pH dependent, enteric polymers that have not been pre-neutralized. Sodium bicarbonate is an especially preferred alkalizing agent. The quantity of alkalizing agent used is directly dependent on the amount of carboxylic acid-bearing monomer present in the pH dependent polymer. Specifically, the alkalizing agent is added in a quantity such that, after reaction with the pH dependent, enteric polymer, 0.1 to 10 mole percent of the acidic groups are present in the salt form. Such amounts and calculations will be apparent to those of ordinary skill without undue experimentation. In cases where the carboxylic acid groups on a polymer have been pre-neutralized prior to use, as is the case with partially-neutralized poly(methacrylic acid, ethyl acrylate) 1:1 sold under the Kollicoat MAE-100P trade name, the use of an alkalizing agent in the film coating composition is not necessary, since the pre-neutralized polymer is already dispersible.

For pH dependent, reverse-enteric polymers comprising amino groups [e.g. poly(butyl methacrylate, 2-dimethylaminoethyl methacrylate, methyl methacrylate) 1:2:1], it is advantageous to include an acidifying agent that makes the polymer more dispersible in water. Inorganic or organic acids may be used including those listed in the aforementioned WO2012/116940 and WO2012/116941. Stearic acid is a preferred acidifying agent for Eudragit E PO [(poly(butyl methacrylate, 2-dimethylaminoethyl methacrylate, methyl methacrylate) 1:2:1]. Sufficient acidifying agent should be added to disperse the reverse-enteric polymer. Generally, the preferred amount of acidifying agent required is in the range of from about 1 to about 20% by weight with respect to the amount of reverse enteric polymer in the formulation. An amount of acidifying agent that is from about 5 to about 15% by weight with respect to the amount of reverse enteric polymer in the formulation is preferred.

A non-limiting list of suitable detackifiers include talc, carnauba wax, hydrogenated castor oil, sodium stearyl fumarate other or mixtures thereof and is used principally to reduce the incidence of tablet sticking that can occur during the film coating of pharmaceutical tablets and the like using aqueous dispersions based on the inventive compositions. In most embodiments, the total detackifier content is from about 0 to about 30% of the dry film coating composition. In some preferred embodiments, it ranges from about 10 to about 25% and more preferably ranges from about 15 to about 20% of the dry film coating composition.

Suitable pigments are those which are FD&C or D&C lakes, titanium dioxide, iron oxides, riboflavin, carmine 40, curcumin, annatto, other non-synthetic colorants, insoluble dyes, pearlescent pigments based on mica and/or titanium dioxide or mixtures thereof. The type and amount of pigment used is dependent upon the desired color will be apparent to those of ordinary skill. Multiple pigments may be used together to create different varying color shades. The total amount of pigment may range from 0 to about 40% by weight of the dry coating composition. In some preferred embodiments, it ranges from about 5 to about 30% and more preferably ranges from about 10-20% of the dry coating composition.

Suitable surfactants will be apparent to those of ordinary skill. In many preferred aspects, however, the surfactant is sodium lauryl sulfate. The surfactant is used principally to reduce the surface tension of the aqueous dispersion prepared from the inventive dry coating composition. The surfactant facilitates droplet spreading and, correspondingly, coating uniformity. In most embodiments, the amount of surfactant used is between 0 and about 5% of the weight of the film coating composition. In some preferred embodiments, it ranges from about 0.1 to about 4% and more preferably ranges from about 0.25 to 3% by weight of the composition.

As one skilled in the art will acknowledge, it is particularly advantageous to incorporate as many of the benefit-imparting additives into the inventive dry powder coating compositions as possible. Therefore, one particularly preferred embodiment of this invention includes compositions comprising: 1) a pH dependent, enteric polymer, preferably about 20 to about 70% by weight of the composition; 2) calcium silicate, preferably about 0.5 to about 15% by weight of the composition; 3) a plasticizer, preferably in the range of about 10% to about 15% by weight of the pH dependent polymer; 4) an alkalizing agent, present in an amount such that between about 0.1 to about 10 mole % of the carboxylic acid groups on the pH dependent polymer will be neutralized; 5) a detackifier, preferably in the range of about 10% to about 25% by weight of the composition; 6) a pigment, preferably in the range of greater than 0% to about 40% by weight of the composition; and 7) a surfactant, preferably in the range of greater than 0% to about 5% by weight of the composition.

Another preferred embodiment of this invention includes compositions comprising: 1) a pH dependent, reverse-enteric polymer, preferably about 20 to about 70% by weight of the composition; 2) calcium silicate, preferably about 0.5 to about 15% by weight of the composition; 3) a plasticizer, preferably in the range of about 10% to about 15% by weight of the pH dependent polymer; 4) an acidifying agent, preferably in the range of about 1 to about 20% by weight of the reverse-enteric polymer; 5) a detackifier, preferably in the range of about 10% to about 25% by weight of the composition; 6) a pigment, preferably in the range of greater than 0% to about 40% by weight of the composition; and 7) a surfactant, preferably in the range of greater than 0% to about 5% by weight of the composition.

Furthermore, the powder mixtures may also include supplemental or auxiliary ingredients typically found in film coatings. A non-limiting list of such adjuvants includes suspension aids, sweeteners, flavorants, etc. and mixtures thereof.

While it is often more advantageous and economical to incorporate as many of the benefit imparting additives into the dry coating composition prior to preparing the aqueous dispersion, it is also possible to add the ingredients stepwise to the aqueous dispersion. For example, one could initially disperse a mixture of pH dependent polymer, calcium silicate and plasticizer in an aqueous medium and then add stepwise the alkalizing agent, detackifier, surfactant and pigment. Furthermore, an anti-foaming agent may be added directly to the aqueous dispersion, if desired, as well.

The powder mixtures are prepared using standard dry blending or mixing techniques known to those of ordinary skill. For example, the ingredients are individually weighed, added to a suitable apparatus and blended for a sufficient time until a substantially uniform mixture of the ingredients is obtained. The time required to achieve such substantial uniformity will, of course, depend upon the batch size and apparatus used. If any of the powder formulation ingredients are liquids, they are added only after all of the dry ingredients have been sufficiently blended, and the combination of wet and dry ingredients is blended for an additional amount of time to ensure homogeneity once all of the liquid is introduced.

In certain embodiments, it is preferable to blend two or more ingredients together as a dry pre-blend. For example, a pre-blend of calcium silicate and plasticizer can be produced on a large scale. The resulting free-flowing powder can then be stored and subsequently used in the production of multiple batches of fully-formulated coating compositions. Advantageously, the pre-blend of calcium silicate and plasticizer can be added quickly to the remaining dry or suspension ingredients including the pH dependent polymer, detackifier, alkalizing agent and pigments, thereby eliminating the need for additional blending time to disperse a liquid plasticizer.

Batch sizes will vary upon need. A non-limiting list of suitable blending devices include diffusion blenders such as a cross flow, V-blender, or hub blender, available from Patterson-Kelly; or convection blenders, such as Ruberg or CVM blenders, available from Azo and Readco, respectively. Blending of the aforementioned formulations may also be achieved by processing ingredients into a granular form to produce a non-dusting granular coating composition by methods including, but not limited to, wet massing, fluid bed granulation, spray granulation and dry compaction, roller compaction or slugging. Other manners of blending will be apparent to those of ordinary skill.

Some preferred dry film coating compositions in accordance with the present invention include:

| Ingredient | % by weight of the composition (unless otherwise noted) | Preferred | More Preferred |
| --- | --- | --- | --- |
| pH dependent Polymer | 20-70 | 25-65 | 30-60 |
| Calcium silicate | 0.5-15 | 1-10 | 3-9 |
| Plasticizer (% by weight of the pH dependent polymer) | 0-20 | 5-18 | 10-15 |

| Ingredient | % by weight of the composition (unless otherwise noted) | Preferred | More Preferred |
|---|---|---|---|
| Alkalizing agent (mole % with respect to carboxylic acid groups on an enteric polymer) | 0.1-10 | — | — |
| Acidifying agent (wt % with respect to reverse-enteric polymer) | 1-20 | 5-15 | — |
| Detackifier | 0-30 | 10-25 | 15-20 |
| Pigments | 0-40 | 5-30 | 10-20 |
| Surfactant (sodium lauryl sulfate) | 0-5 | 0.1-4 | 0.25-3 |
| Other auxiliary ingredients | 0-20 | — | — |

It will be understood from the foregoing table that the preferred dry film coating compositions will include at least a pH dependent polymer and calcium silicate as described herein. The additional ingredients, if included, will cause the amount of pH dependent polymer, calcium silicate and plasticizer to be reduced but still within the ranges described herein so that the total amount of all ingredients in the dry blend will be 100% by weight.

For purposes of illustration and not limitation, an aqueous dispersion having about 20% solids content can be formed by dispersing 80 grams of a blended powder mixture described hereinabove into 320 grams of ambient temperature water. The water is weighed into a suitable vessel, i.e. one with a diameter approximately equal to the depth of the final suspension. A low shear mixer, preferably one having a mixing blade with a diameter about one third the diameter of the mixing vessel, is lowered into the water and turned on to create a vortex from the edge of the vessel down to about just above the mixing blade to prevent entrapment of air. The 80 grams of dry film coating composition is added to the vortex at a rate where there is no excessive buildup of dry powder. The speed and depth of the mixing blade is adjusted to avoid air being drawn into the suspension so as to avoid foaming. The suspension is stirred at low speed, preferably 350 rpm or less, for a time sufficient to ensure that a homogenous mixture is formed. Using the above batch size as a guide, about 45 minutes mixing time is required. The suspension is then ready for spraying onto pharmaceutical substrates and the like. Those of ordinary skill will also realize that there are many ways of preparing a substantially homogenous mixture of the solids in water and that the scope of the invention is in no way dependent on the apparatus used.

As mentioned previously, it is also possible to add the optional ingredients stepwise to the aqueous dispersion. For example, one could initially disperse a mixture of pH dependent polymer, calcium silicate and plasticizer in an aqueous medium and then add stepwise alkalizing agent, detackifier, surfactant and pigment using the same equipment as described above.

In still further embodiments of the invention, there are provided orally-ingestible substrates coated with the inventive film coating formulations. The coated substrates have excellent appearance and uniformity, resistance to agglomeration and desirable delayed release properties.

As will be described in the examples below, the methods include applying the film coating compositions as aqueous suspensions to the surfaces of orally ingestible substrates. The film coating can be applied as part of a pan coating or spray coating process commonly used to coat such articles. The amount of coating applied will depend upon several factors, including the nature and functionality of the film coating, the substrate to be coated and the apparatus employed to apply the coating, etc. For delayed release coatings on standard tablets of about 11 mm in diameter, a desirable weight gain would be a theoretical weight gain of between about 5 and about 12%, and more preferably between about 6 and about 10%. For coatings applied to multiparticulates (i.e. drug layered beads or fine particle active ingredients themselves), substantially higher weight gains of the coating are required since the surface area of the substrates is much greater than the standard tablet mentioned above. In these cases, a weight of 20-40% is often desirable.

In some embodiments of the invention, the amount of film coating containing calcium silicate required to achieve sufficient enteric or delayed release properties after ingestion is reduced by about 10 to about 20% or more as compared to prior art compositions. The advantages associated with using the inventive film coating formulations include reduced processing times, lower material costs and consumption.

The coated, orally-ingestible substrates described above can also include a subcoat film coating between the orally-ingestible substrate and the inventive film coating composition. The subcoat selected is preferably based on an edible film coating composition that is compatible with and adheres to both the orally-ingestible substrate and the inventive coating. Thus, the artisan may choose from a wide variety of pharmaceutical or food-acceptable coatings for use as subcoats in the present invention. The subcoat is also applied to the substrate to provide from about a 0.25 to about a 5.0% weight gain to the orally-ingestible substrate.

A non-limiting list of suitable substrates that can be coated with the inventive coating system include compressed tablets, caplets, cores including pharmaceuticals, drug-layered sugar spheres or similar beads, nutraceuticals and dietary supplements as well as any other art-recognized orally ingestible core.

EXAMPLES

The following examples serve to provide further appreciation of the invention but are not meant in any way to restrict the effective scope of the invention. All ingredients are expressed as being by weight %.

Example 1

I. Polymer Blend

Aspirin cores (2.5 kg total charge; 325 mg aspirin per tablet) were coated sequentially with a sub-coating dispersion made from an Opadry® coating composition based on hypromellose (HPMC) and an inventive enteric coating suspension prepared as described below. First, the Opadry subcoating dispersion was prepared by adding the dry Opadry formula (75 grams) to deionized water (606.8 grams) and stirring this combination with a propeller mixer for 45 minutes. A homogeneous dispersion was thus obtained. The inventive enteric, dry powder composition was prepared by thoroughly mixing Eudragit® L100-55 (137.5 grams; 55.0 wt %), sodium bicarbonate (2.8 grams; 1.1 wt %), talc (44.5 grams; 17.8 wt %), titanium dioxide (32.5 grams; 13.0 wt %), calcium silicate (10.0 grams; 4.0 wt %), sodium lauryl sulfate (1.3 grams; 0.5 wt %), carnauba wax (5.0 grams; 2.0 wt %) in a food processor for five minutes. To this solid mixture was added triethyl citrate (16.5 grams; 6.6 wt %). After an additional two minutes of mixing, a homogeneous, free-flowing powder with no visible agglomerates was obtained.

II. Suspension

An enteric suspension was then prepared by first mixing an aqueous silicon emulsion (Anti-foam FG-10; 1 gram) into deionized water (1.0 kg) using a low shear mixer, having a mixing blade with a diameter about one third the diameter of the mixing vessel, lowered into the water and turned on to create a vortex from the edge of the vessel down to about just above the mixing blade to prevent entrapment of air. After mixing the anti-foam for 30 seconds, the 250 grams of an inventive dry film coating composition was added to the vortex at a rate where there was no excessive buildup of dry powder. The speed and depth of the mixing blade was adjusted to avoid air being drawn into the suspension so as to avoid foaming. The suspension was stirred at low speed, 350 rpm or less, for a time sufficient to ensure that a homogenous mixture was formed. About 45 minutes mixing time was required. To a 15 inch diameter O'Hara LabCoat 1 coating pan, equipped with a Watson Marlow peristaltic pump with one pump head, platinum-cured silicone tubing (size 15) and one Spraying Systems spray gun (⅛" VAU SS; fluid nozzle-VF60100-SS; air cap-VA1282125-60-SS), were added aspirin cores (2.5 kg total charge; 325 mg of aspirin per tablet). The tablets were sequentially coated with the Opadry subcoating dispersion and the inventive, enteric coating suspension under the following process conditions:

| Coating Process Parameters (15" O'Hara LabCoat 1) | | |
|---|---|---|
| | Subcoat | Enteric Coat |
| Fluid delivery rate (g/min) | 18 | 22 |
| Atomizing air pressure (psi) | 18 | 18 |
| Pattern air pressure (psi) | 20 | 20 |
| Tablet bed temperature (° C.) | 43 | 30 |
| Pan speed (RPM) | 17 | 17 |

No tackiness or tablet-to-tablet sticking was observed during the coating run.

The final coated tablets were evaluated using USP Dissolution Method <711> according to the "delayed-release" aspirin monograph. As prescribed by this method, six of the coated tablets were placed in 0.1 N HCl for two hours at 37° C. The release in the acid phase of the test after two hours was 0%, as compared with the upper limit of 10%. The six tablets were then placed in phosphate buffer (pH=6.8), and the amount of aspirin released after 90 minutes was greater than 80% in 35 minutes, as compared to the compendial requirement of not less than 80% released after 90 minutes. The final coated tablets were also evaluated using a USP Dissolution Method <711> according to the "delayed-release" aspirin monograph modified by placing six tablets coated in pH 4.5 acetate buffer for two hours at 37° C. to investigate intermediate pH performance. The release in the acid phase of the test after two hours was 0%, as compared with the upper limit of 10%. The six tablets were then placed in phosphate buffer (pH=6.8), and the amount of aspirin released after 90 minutes was greater than 80% in 35 minutes, as compared to the compendial requirement of not less than 80% released after 90 minutes.

The final coated tablets were also evaluated using a modified version of USP Disintegration Method <701>. Fifty tablets were stressed for 100 revolutions in a friabilator. Then, 50 stressed and 50 unstressed tablets were placed in a basket assembly and immersed for one hour in simulated gastric fluid (0.1 N HCl). The basket was moved up and down in the simulated gastric fluid at a rate of about 29-32 cycles/minute. The integrity of the tablets was evaluated after removal from the simulated gastric fluid. In both cases (stressed and unstressed), none of the tablets exhibited signs of bloating, cracks or fissures. The final coated tablets were also examined qualitatively. The resulting coating was smooth and uniform and showed no evidence of chipping, peeling or color non-uniformity.

Example 2

In another preparation, a partial pre-blend of components of the inventive enteric, dry powder composition of Example 1 was prepared by thoroughly mixing talc (626.8 grams; 62.68 wt %) and calcium silicate (140.8 grams; 14.08 wt %) in a food processor for five minutes. To this solid mixture was added triethyl citrate (232.4 grams; 23.24 wt %). After an additional two minutes of mixing, a homogeneous, free-flowing powder with no visible agglomerates was obtained.

Example 3

The dry film coating composition of Example 3 was prepared by thoroughly mixing Eudragit® L100-55 (137.5 grams; 55.0 wt %), sodium bicarbonate (2.8 grams; 1.1 wt %), titanium dioxide (32.5 grams; 13.0 wt %), sodium lauryl sulfate (1.3 grams; 0.5 wt %), carnauba wax (5.0 grams; 2.0 wt %) and the pre-blend of Example 2 (71 g; 28.4 wt %) in a food processor for five minutes. A homogeneous, free-flowing powder with no visible agglomerates was obtained.

The inventive enteric suspension was then coated as described in Example 1, II. No tackiness or tablet-to-tablet sticking was observed during the coating run.

The final coated tablets were evaluated using USP Dissolution Method <711> according to the "delayed-release" aspirin monograph. The release in the acid phase of the test after two hours was 0%, as compared with the upper limit of 10%. The six tablets were then placed in phosphate buffer (pH=6.8), and the amount of aspirin released after 90 minutes was greater than 80% in 35 minutes, as compared to the compendial requirement of not less than 80% released after 90 minutes.

Comparative Examples (A-G)

To provide evidence that the inclusion of calcium silicate in pH dependent film coating compositions reduces the tendency for agglomeration of the dry film coating composition and improves the delayed release properties of the pH dependent polymer at relatively low weight gains, a series of evaluations were conducted on formulations with and without the inclusion of calcium silicate. The substrate used, suspension preparation and coating processes for these examples correspond to those described in Example 1. Only the coating compositions varied. To evaluate pH dependent performance, the coated tablets in each example were individually weighed and placed in an intermediate pH (acetate buffer USP, pH 4.5) for 2 hours in a disintegration bath (Erweka ZT44), after which they were removed and inspected for bloating or discoloration. Tablets were dried using a tissue paper and reweighed. The percent weight difference, before and after exposure to acid, was reported as the acid uptake value.

Example 4

A similar formulation was utilized as in Example 1 except that the carnauba wax was removed from the formulation, and talc and titanium dioxide levels were increased. The formulations and results corresponding to Comparative Example A and Example 4 are reported in the following table.

|  | Wt % in 300 grams | |
| --- | --- | --- |
| Components | Comparative Example A | Example 4 |
| Eudragit L100-55 | 55.0 | 55.0 |
| Calcium silicate | 0.0 | 4.0 |
| Talc | 21.8 | 22.8 |
| Titanium dioxide | 15.0 | 10.0 |
| Triethyl citrate | 6.6 | 6.6 |
| Sodium bicarbonate | 1.1 | 1.1 |
| Sodium lauryl sulfate | 0.5 | 0.5 |
|  | 100.0 | 100.0 |
| Tablet appearance and % fluid uptake in pH 4.5 acetate buffer (n = 6) | | |
| 5% weight gain | failed, all bloated | passed, 5.5% |
| 6% weight gain | failed, all bloated | passed, 5.43% |
| 8% weight gain | failed, all bloated | passed, 5.37% |
| 10% weight gain | failed 1 soft, 7.2% for n = 5 | passed, 5.37% |

It is apparent from the above result that the use of calcium silicate enables the coated tablets to pass the pH 4.5 (enteric) testing at all weight gains versus the formulation without calcium silicate, which fails the testing at all weight gains.

Example 5

A similar formulation was utilized as in Example 1 except that it was pigmented using an aluminum lake. Further disintegration test results in pH 6.8 phosphate buffer are also shown. The formulations and results corresponding to Comparative Example B and Example 5 are reported in the following table.

|  | Wt % in 300 grams | |
| --- | --- | --- |
| Components | Comparative Example B | Example 5 |
| Eudragit L100-55 | 55.0 | 55.0 |
| Calcium silicate | 0.0 | 4.0 |
| Talc | 21.8 | 17.8 |
| Carnauba wax | 2.0 | 2.0 |
| Yellow #6 aluminum lake | 3.0 | 3.0 |
| Titanium dioxide | 10.0 | 10.0 |
| Triethyl citrate | 6.6 | 6.6 |
| Sodium bicarbonate | 1.1 | 1.1 |
| Sodium lauryl sulfate | 0.5 | 0.5 |
|  | 100.0 | 100.0 |
| Tablet appearance and % fluid uptake after 2 hours in pH 4.5 acetate buffer (n = 6) | | |
| 6% weight gain | failed, all bloated | passed, 5.98% |
| 8% weight gain | failed, 3 bloated | passed, 5.90% |
| 10% weight gain | failed 1 bloated, 5.93% for n = 5 | Passed, 5.88% |
| Disintegration time (minutes) in pH 6.8 phosphate buffer | | |
| 6% weight gain | 9 | 10 |
| 8% weight gain | 10 | 13 |
| 10% weight gain | 15 | 18 |

It is apparent from the above result that the use of calcium silicate enables consistent passing enteric performance at significantly less coating weight gain than the formulation without calcium silicate when including aluminum lake pigments. It is also shown that the addition of calcium silicate does not significantly impact the disintegration time of the tablet in pH 6.8 phosphate buffer.

Example 6

A similar formulation was utilized as in Example 1 except that it incorporated an iron oxide pigment. The formulations and results corresponding to Comparative Example C and Example 6 are reported in the following table.

|  | Wt % in 300 grams | |
| --- | --- | --- |
| Components | Comparative Example C | Example 6 |
| Eudragit L100-55 | 55.0 | 55.0 |
| Calcium silicate | 0.0 | 4.0 |
| Talc | 21.8 | 17.8 |
| Carnauba wax | 2.0 | 2.0 |
| Yellow iron oxide | 3.0 | 3.0 |
| Titanium dioxide | 10.0 | 10.0 |
| Triethyl citrate | 6.6 | 6.6 |
| Sodium bicarbonate | 1.1 | 1.1 |
| Sodium lauryl sulfate | 0.5 | 0.5 |
|  | 100.0 | 100.0 |
| Tablet appearance and % fluid uptake after 2 hours in pH 4.5 acetate buffer (n = 6) | | |
| 6% weight gain | failed, 3 bloated | passed, 4.84% |
| 8% weight gain | failed 1 bloated, 5.08% for n = 5 | passed, 4.88% |
| 10% weight gain | passed, 4.94% | passed, 5.10% |

It is apparent from the above result that the use of calcium silicate enables consistent passing enteric performance at significantly less coating weight gain than the formulation without calcium silicate when including iron oxide pigments.

Example 7

A similar formulation was utilized as in Example 1 except that it incorporated a higher level of sodium bicarbonate as a neutralization agent. The formulations and results corresponding to Comparative Example D and Example 7 are reported in the following table.

|  | Wt % in 300 grams | |
| --- | --- | --- |
| Components | Comparative Example D | Example 7 |
| Eudragit L100-55 | 55.0 | 55.0 |
| Calcium silicate | 0.0 | 4.0 |
| Talc | 21.3 | 17.3 |
| Carnauba wax | 2.0 | 2.0 |
| Yellow iron oxide | 3.0 | 3.0 |
| Titanium dioxide | 10.0 | 10.0 |
| Triethyl citrate | 6.6 | 6.6 |
| Sodium bicarbonate | 1.7 | 1.7 |
| Sodium lauryl sulfate | 0.5 | 0.5 |
|  | 100.0 | 100.0 |
| Tablet appearance and % fluid uptake after 2 hours in pH 4.5 acetate buffer (n = 6) | | |
| 6% weight gain | failed, all bloated | passed, 5.80% |
| 8% weight gain | failed, all bloated | passed, 6.25% |
| 10% weight gain | failed, all bloated | passed, 6.75% |

It is apparent from the above result that the use of calcium silicate enables consistent passing enteric performance at significantly less coating weight gain than the formulation without calcium silicate. This example uses a higher level of neutralization (sodium bicarbonate) with respect to polymer level than the previous examples. It was expected that testing failures would be observed at higher sodium bicarbonate use levels; however, the formulation with calcium silicate was surprisingly still resistant to pH 4.5 acetate buffer while the formulation without calcium silicate was not.

Example 8

A similar formulation was utilized as in Example 4 except that it incorporated a higher polymer level, higher level of sodium bicarbonate as a neutralization agent and no pigments. The formulations and results corresponding to Comparative Example E and Example 8 are reported in the following table.

| | Wt % in 300 grams | |
|---|---|---|
| Components | Comparative Example E | Example 8 |
| Eudragit L100-55 | 60.0 | 57.5 |
| Calcium silicate | 0.0 | 4.2 |
| Colloidal silicon dioxide | 1.3 | 1.2 |
| Talc | 29.3 | 28.0 |
| Triethyl citrate | 7.2 | 6.9 |
| Sodium bicarbonate | 1.8 | 1.7 |
| Sodium lauryl sulfate | 0.5 | 0.5 |
| | 100.0 | 100.0 |
| Tablet appearance and % fluid uptake after 2 hours in pH 4.5 acetate buffer (n = 6) | | |
| 5% weight gain | failed, 5 bloated | passed, 6.03% |
| 6% weight gain | failed, all bloated | passed, 6.5% |
| 8% weight gain | failed, 3 bloated | passed, 6.44% |
| 10% weight gain | failed, 3 bloated | passed, 7.09% |

It is apparent from the above result that the use of calcium silicate enables consistent passing enteric performance at significantly less coating weight gain than the formulation without calcium silicate in formulations using a higher polymer level, higher level of sodium bicarbonate as a neutralization agent and no pigments.

Example 9

A similar formulation was utilized as in Example 4 except that it incorporated Kollicoat MAE 100P (pre-neutralized methacrylic acid/ethyl acrylate co-polymer). Therefore, sodium bicarbonate (neutralization agent) was removed from the formulation. Comparative Example F is an analogous formulation with no calcium silicate. The formulations and results corresponding to Comparative Examples F and Example 9 are reported in the following table.

| | Wt % in 300 grams | |
|---|---|---|
| Components | Comparative Example F | Example 9 |
| Kollicoat MAE 100P | 55.0 | 55.0 |
| Calcium silicate | 0.00 | 4.0 |
| Talc | 24.9 | 20.9 |
| Triethyl citrate | 6.6 | 6.6 |
| Titanium dioxide | 13.00 | 13.0 |
| Sodium lauryl sulfate | 0.5 | 0.5 |
| | 100.0 | 100.0 |
| Tablet appearance and % fluid uptake after 2 hours in pH 4.5 acetate buffer (n = 6) | | |
| 5% weight gain | failed, all bloated | passed, 7.5% |
| 6% weight gain | failed, 4 bloated | passed, 7.8% |
| 8% weight gain | failed, 4 bloated | passed, 8.1% |
| 10% weight gain | failed, 4 bloated | passed, 8.29% |

It is apparent from the above result that the use of the pre-neutralized Kollicoat MAE 100P polymer in the inventive formulation provides passing enteric performance in intermediate pH media while the comparative formulation does not.

Example 10

To provide further evidence that the calcium silicate is acting as a reversible plasticizer sequestrant in pH dependent film coating compositions and reduces the tendency for agglomeration of the dry film coating composition, the formulation of Example 8 was modified using Eudragit E PO (copolymer based on dimethylaminoethyl methacrylate, butyl methacrylate, and methyl methacrylate). This polymer has a glass transition temperature (Tg) of about 48° C. and, when combined with an acidifying agent (stearic acid), is susceptible to powder agglomeration when stored at elevated environmental conditions. Both the inventive formulation (with calcium silicate) and the comparative formulation without calcium silicate were stored in low density polyethylene, sealed bags for seven weeks in 30° C./65% RH conditions. Powder agglomeration was tested by placing powders onto a sieve set and shaking for 10 minutes using a Ro-Tap sieve shaker. The formulations and results corresponding to Comparative Examples G and Example 10 are reported in the following table.

| | Wt % in 500 grams | |
|---|---|---|
| Components | Comparative Example G | Example 10 |
| Eudragit E PO | 62.5 | 62.5 |
| Calcium Silicate | 0.0 | 5.0 |
| Talc | 15.0 | 10.0 |
| Stearic Acid | 9.4 | 9.4 |
| SLS | 6.3 | 6.3 |
| Sodium CMC | 5.0 | 5.0 |
| Cabosil | 1.8 | 1.8 |
| | 100.0 | 100.0 |
| Screen analysis of product stored at 30° C./65% RH for 7 weeks | | |
| % retained on 5 mesh (4000µ) | 97.5 | 0.0 |
| % retained on 18 mesh (1000µ) | 0.6 | 0.0 |
| % retained on 25 mesh (710µ) | 0.1 | 0.0 |
| % Through 25 mesh (710µ) | 1.8 | 100.0 |

The inventive formulation containing calcium silicate remained a flowable powder after storage at elevated environmental conditions and easily passed through the 25 mesh sieve indicating no powder agglomerates >710µ, (microns). The comparative formulation after storage was fused into a semi-solid aggregate in which most material would not pass through a 5 mesh sieve during the shaking process.

Examples 11-15 and Comparative Example H

Formulations were prepared with calcium silicate levels varying from 0.25% to 10% as shown in the table below. The aspirin cores, suspension preparation method and coating process for these examples were the same as those described in Example 1. The formulations and results are reported in the following table.

| | Wt % in 300 grams | | |
|---|---|---|---|
| Components | Comparative Example H | Example 11 | Example 12 |
| Eudragit L100-55 | 60.00 | 60.00 | 60.00 |
| Calcium silicate | 0.25 | 0.50 | 1.00 |
| Talc | 17.85 | 17.60 | 19.6 |
| Carnauba wax | 0.00 | 0.00 | 0.50 |
| Titanium dioxide | 13.00 | 13.00 | 10.00 |
| Triethyl citrate | 7.20 | 7.20 | 7.20 |
| Sodium bicarbonate | 1.20 | 1.20 | 1.20 |
| Sodium lauryl sulfate | 0.50 | 0.50 | 0.50 |
| | 100.00 | 100.00 | 100.00 |
| Tablet appearance and % fluid uptake after 2 hours in pH 4.5 acetate buffer (n = 6) | | | |
| 6% weight gain | failed, 6 bloated | failed, 4 bloated | failed, 5 bloated |
| 8% weight gain | failed, 6 bloated | failed, 1 bloated | failed, 2 bloated |
| 10% weight gain | failed, 3 bloated | passed, 6.9% | passed, 6.05% |

| | Wt % in 300 grams | | |
|---|---|---|---|
| Components | Example 13 | Example 14 | Example 15 |
| Eudragit L100-55 | 62.20 | 62.00 | 55.0 |
| Calcium silicate | 3.00 | 4.00 | 10.0 |
| Talc | 10.00 | 9.82 | 13.8 |
| Titanium dioxide | 15.00 | 15.00 | 15.0 |
| Triethyl citrate | 8.08 | 7.44 | 6.6 |
| Sodium bicarbonate | 1.22 | 1.24 | 1.1 |
| Sodium lauryl sulfate | 0.50 | 0.50 | 0.5 |
| | 100.00 | 100.00 | 100.0 |
| Tablet appearance and % fluid uptake after 2 hours in pH 4.5 acetate buffer (n = 6) | | | |
| 6% weight gain | passed, 4.9% | passed, 5.48% | failed, 1 bloated |
| 8% weight gain | passed, 5.03% | passed, 5.47% | passed, 7.98% |
| 10% weight gain | passed, 4.9% | passed, 5.67% | passed, 7.90% |

The above results show that as little as 0.5% calcium silicate in the inventive film coating formulations provides passing enteric performance at a 10% coating weight gain. Also of note is that when the level of calcium silicate is increased to 3% or greater, passing enteric performance is achieved at lower coating weight gains, i.e. less than 10% which save processing time and materials.

Example 16

The dry film coating composition of Example 1 was stored for three months at 40° C. and 75% relative humidity. After this time, the composition was still free flowing with no visible agglomerates. The aged film coating was then dispersed in water and coated onto aspirin tablets as described in Example 1. The resulting coated aspirin tablets had similar disintegration and dissolution properties as those obtained in Example 1 indicating that dry film coating composition was stable over time even when stored under stressed environmental conditions.

Example 17

A formulation similar to Example 4 was prepared except that dibutyl sebacate was used in place of triethyl citrate as plasticizer. The components of the formulation were Eudragit L100-55 (165 grams; 55%), calcium silicate (12 grams; 4%), talc (59.4 grams; 19.8%), titanium dioxide (7.15 grams; 13%), dibutyl sebacate (19.8 grams; 6.6%), sodium bicarbonate (3.3 grams; 1.1%) and sodium lauryl sulfate (1.5 grams; 0.5%). The aspirin cores, suspension preparation method and coating process were the same as those described in Example 1. When the aspirin tablets were immersed in pH 4.5 acetate buffer for two hours, coated tablets containing 6, 8 and 10% weight gain of the film coating composition (6 tablets at each weight gain increment) passed the testing with no signs of bloating, cracking or premature disintegration. The fluid uptake for the coated tablets was 5.07, 5.10 and 5.23% for tablets containing 6, 8 and 10% weight gains of the coating, respectively.

Examples 18 and 19; Comparative Examples I and J

Formulations comparable to Examples 4 and 9 were prepared, but poloxamer 407 was used instead of triethyl citrate as plasticizer. Comparative examples I and J, without calcium silicate, were also prepared. The suspension preparation method, coating process and testing protocol in pH 4.5 acetate buffer were the same as those described in Example 1; however, in these examples, placebo tablets rather than aspirin tablets were used.

| | Wt % in 300 grams | | | |
|---|---|---|---|---|
| Components | Comparative Example I | Example 18 | Comparative Example J | Example 19 |
| Eudragit L100-55 | 55.00 | 55.00 | | |
| Kollicoat MAE 100P | | | 55.0 | 55.0 |
| Calcium silicate | 0.00 | 4.00 | 0.00 | 4.0 |
| Talc | 23.25 | 19.25 | 24.9 | 20.9 |
| Titanium dioxide | 13.00 | 13.00 | 13.0 | 13.0 |
| Poloxamer 407 | 6.60 | 6.60 | 6.6 | 6.6 |
| Sodium bicarbonate | 1.65 | 1.65 | | |
| Sodium lauryl sulfate | 0.5 | 0.50 | 0.50 | 0.5 |
| | 100.00 | 100.00 | 100.0 | 100.0 |
| Tablet appearance and % fluid uptake after 2 hours in pH 4.5 acetate buffer | | | | |
| 6% weight gain | failed, 6 bloated | passed, 9.22% | failed, 6 bloated | passed, 9.62% |
| 8% weight gain | failed, 6 bloated | passed, 11.0% | failed, 6 bloated | passed, 10.85% |
| 10% weight gain | failed, 6 bloated | passed, 12.0% | failed, 6 bloated | passed, 11.9% |

Placebo tablets coated with the formulations of Examples 18 and 19, comprising calcium silicate, passed the testing in pH 4.5 acetate buffer at all weight gains; whereas, Comparative Examples I and J, without calcium silicate, failed the testing at all weight gains.

Example 20 and Comparative Example K

The following coating formulations comprising poloxamer 407 were prepared and assessed for relative stability. The formulations were placed into polyethylene bags and stored at 40° C. and 75% relative humidity (RH) for 7 weeks. The formulations were then passed through screens containing openings of decreasing size (5 mesh through 25 mesh U.S. standard sizes) to assess the extent of agglomeration of the powders. This was done by placing the powders onto the sieve set and shaking for 10 minutes using a Ro-Tap sieve shaker. Agglomerates having sizes larger than the screen openings were quantified as "% retained" relative to the total amount of powder being screened. The formulations were also coated onto placebo tablets to a 10% weight gain as described in Example 1. The coated tablets were packaged in polyethylene bottles and stored at 40° C. and 75% RH for 2 months. The coated tablets were examined at 1 week, 2 weeks, 1 month and 2 months for signs of sticking or blocking (tablet-to-tablet agglomeration).

| Components | Comparative Example K | Example 20 |
|---|---|---|
| Eudragit L100-55 | 55.00 | 55.00 |
| Calcium silicate | 0.00 | 4.00 |
| Talc | 23.8 | 19.8 |
| Titanium dioxide | 13.00 | 13.00 |
| Poloxamer 407 | 6.60 | 6.60 |
| Sodium bicarbonate | 1.1 | 1.1 |
| Sodium lauryl sulfate | 0.5 | 0.50 |
| | 100.00 | 100.00 |
| Screen analysis of coating formulations after storage at 40° C./75% RH for 7 weeks | | |
| % retained on 5 mesh (4000 microns) | 11.61 | 0.0 |
| % retained on 18 mesh (1000 microns) | 6.22 | 0.0 |
| % retained on 25 mesh (710 microns) | 3.11 | 0.0 |
| % through 25 mesh | 79.06 | 100.0 |
| Coated tablet (10% weight gain) sticking or blocking after storage at 40° C./75% RH | | |
| 1 week | Yes | No |
| 2 weeks | Yes | No |
| 1 month | Yes | No |
| 2 months | Yes | No |

The formulation comprising calcium silicate showed no signs of agglomeration either as a powder or when coated onto placebo tablets. In contrast, the formulation without calcium silicate agglomerated in powder form and when coated onto placebo tablets.

Example 21

Suglets® sugar spheres were drug layered with lansoprazole and coated sequentially with a sub-coating dispersion made from an Opadry® coating composition based on hypromellose (HPMC) and a coating suspension made from the coating formulation of Example 20. First, the Opadry sub-coating dispersion was prepared by adding the dry Opadry formula (125 grams) to deionized water (1125 grams) and stirring this combination with a propeller mixer for 45 minutes. A homogeneous dispersion was thus obtained. An enteric suspension was then prepared by first mixing an aqueous silicon emulsion (Anti-foam FG-10; 5 gram) into deionized water (5.0 kg) using a low shear mixer, preferably one having a mixing blade with a diameter about one third the diameter of the mixing vessel, lowered into the water and turned on to create a vortex from the edge of the vessel down to about just above the mixing blade to prevent entrapment of air. After mixing the anti-foam for 30 seconds, 1 kg of the film coating composition of Example 21 was added to the vortex at a rate where there was no excessive build-up of dry powder. The speed and depth of the mixing blade was adjusted to avoid air being drawn into the suspension so as to avoid foaming. The suspension was stirred at low speed (350 rpm or less) for a time sufficient to ensure that a homogenous mixture was formed. About 45 minutes mixing time was required. To a Glatt GPCG-2 fluid bed coater, equipped with a 7-inch Wurster insert, one pump head, silicone tubing (size 16) and one Spraying Systems spray gun (1.2 mm fluid nozzle 515817; nozzle head W15826; nozzle tube W54602) were added lansoprazole drug-layered Suglets (2.5 kg total charge; 15 mg of lansoprazole per gram sugar sphere). The drug layered multiparticulates were sequentially coated with the Opadry sub-coating dispersion and the inventive, enteric coating suspension under the following process conditions:

| Coating Process Parameters (Glatt GPCG-2, 7-inchWurster) | | |
|---|---|---|
| | Subcoat | Enteric Coat |
| Fluid delivery rate (g/min) | 10 | 15 |
| Atomizing air pressure (bar) | 2 | 2 |
| Air velocity (m$^3$/h) | 130 | 130 |
| Product temperature (° C.) | 45 | 35 |

No tackiness or bead-to-bead sticking was observed during the coating run.

The final coated multiparticulates were evaluated using USP Dissolution Method <711> according to the "delayed-release" lansoprazole monograph. As prescribed by this method, six separate one gram samples of the coated multiparticulates were placed in 0.1 N HCl for one hour at 37° C. The release in the acid phase of the test after one hour was 1%, as compared with the upper limit of 10%. The multiparticulates were then placed in phosphate buffer (pH=6.8), and the amount of lansoprazole released after 60 minutes was greater than 85% in 20 minutes, as compared to the compendial requirement of not less than 85% released after 60 minutes. The final coated multiparticulates were also evaluated using a USP Dissolution Method <711> according to the "delayed-release" lansoprazole monograph modified by placing six separate one gram samples of the coated multiparticulates in pH 4.5 acetate buffer for one hour at 37° C. to investigate intermediate pH performance. The release in the acid phase of the test after one hour was 3%, as compared with the upper limit of 10%. The multiparticulates were then placed in phosphate buffer (pH=6.8), and the amount of lansoprazole released after 60 minutes was 100%, as compared to the compendial requirement of not less than 85% released after 60 minutes.

Example 22 and Comparative Example L

The methods employed in Example 22 were repeated while using the formulations in the following table:

| Components | Comparative Example L | Example 22 |
|---|---|---|
| Eudragit L100-55 | 55.0 | 55.0 |
| Calcium silicate | 0.0 | 4.0 |
| Talc | 21.8 | 17.8 |
| Titanium dioxide | 13.0 | 13.0 |
| Triethyl citrate | 6.6 | 6.6 |
| Carnauba wax | 2.0 | 2.0 |
| Sodium bicarbonate | 1.1 | 1.1 |
| Sodium lauryl sulfate | 0.5 | 0.5 |
| | 100.0 | 100.0 |

For Example 22, less than or equal to 3% lansoprazole was released in both pH 1 and pH 4.5 media, and 96% of lansoprazole was released in the pH 6.8 medium. All testing met compendial requirements. For Comparative Example L, without calcium silicate, the coated lansoprazole sugar spheres did not meet the compendial testing requirements in the pH 1 medium—52% of lansoprazole was released after 60 minutes versus the upper limit of 10%.

Example 23

The procedures of Example 1 are repeated but with a different formulation comprising 20 parts Eudragit L100-55, 40 parts talc, 22 parts titanium dioxide, 15 parts calcium silicate, 2 parts poloxamer 407, 0.5 part sodium bicarbonate and 0.5 part sodium lauryl sulfate.

Example 24

The procedures of Example 1 are repeated but with a different formulation comprising 70 parts Eudragit L100-55, 12.6 parts talc, 5 parts calcium silicate, 8 parts poloxamer 407, 1.4 parts sodium bicarbonate and 3.0 parts sodium lauryl sulfate.

What is claimed is:

1. A film coating composition comprising a pH dependent enteric polymer, a plasticizer, and from about 3 to about 9% by weight calcium silicate, the amount of calcium silicate being sufficient to reversibly sequester the plasticizer from the pH dependent enteric polymer while the film coating composition is in the dry state.

2. The composition of claim 1 wherein the enteric polymer is selected from the group consisting of polyvinylacetate phthalate, hydroxypropylmethyl cellulose acetate succinate, hydroxypropylmethyl cellulose phthalate, cellulose acetate phthalate, poly(methacrylic acid, methyl methacrylate) 1:1, poly(methacrylic acid, ethyl acrylate) 1:1, partially-neutralized poly(methacrylic acid, ethyl acrylate) 1:1, and poly(methacrylic acid, methyl methacrylate) 1:2 and mixtures thereof.

3. The composition of claim 1 wherein the pH dependent polymer comprises 20-70% by weight of the composition.

4. The composition of claim 1 wherein the calcium silicate has a surface area of 50 m²/gram or greater.

5. The composition of claim 4 wherein the calcium silicate has a surface area of 120 m²/gram or greater.

6. The composition of claim 4 wherein the calcium silicate has a surface area of 250 m²/gram or greater.

7. The composition of claim 1 wherein the calcium silicate comprises about 3-8% of the composition.

8. The composition of claim 1 wherein the plasticizer is selected from the group consisting of triethyl citrate, tributyl citrate, glyceryl triacetate, acetyltriethyl citrate, dibutyl sebacate, diethyl phthalate, polyethylene glycol having a molecular weight in the range of 200 to 8000, glycerol, castor oil, copolymers of propylene oxide and ethylene oxide, poloxamers and mixtures thereof.

9. The composition of claim 1 wherein the amount of plasticizer is about 5-20% by weight of the pH dependent enteric polymer used.

10. The composition of claim 9 wherein the amount of plasticizer is about 7-18% by weight of the pH dependent enteric polymer used.

11. The composition of claim 10 wherein the amount of plasticizer is about 10-15% by weight of the pH dependent enteric polymer used.

12. The composition of claim 1 wherein the plasticizer is triethyl citrate or a poloxamer.

13. The composition of claim 2, wherein the pH dependent enteric polymer is poly(methacrylic acid, ethyl acrylate) 1:1, the plasticizer is a poloxamer; and the composition further comprises sodium bicarbonate, talc and/or carnauba wax and sodium lauryl sulfate.

14. An aqueous suspension comprising the composition of claim 1 and water.

15. The aqueous suspension of claim 14 further comprising one or more of an alkalizing agent, an acidifying agent, a detackifier, a pigment and a surfactant.

16. An orally-ingestible substrate coated with the aqueous suspension of claim 14.

17. A method of making an aqueous film coating dispersion, comprising:
dispersing the enteric film coating composition of claim 1 in water at ambient temperature.

18. The method of claim 17 further comprising the step of coating said aqueous dispersion onto orally-ingestible substrates.

19. A dry film coating composition, comprising a pH-dependent enteric polymer, an amount of a plasticizer sufficient for plasticizing said pH-dependent enteric polymer and from about 3 to about 9% by weight calcium silicate, the amount of calcium silicate being sufficient to reversibly sequester said plasticizer from said pH-dependent polymer while in the dry state; and
wherein when the film coating composition is coated on a tablet to a weight gain of between about 6 and about 10% by weight, the amount of tablet content released after two hours is less than 10% by weight.

20. The method of claim 17, further comprising combining one or more of an alkalizing agent, a detackifier, a pigment and a surfactant, separately to the aqueous suspension.

21. The method of claim 17, wherein the dry, pH dependent enteric film coating composition of claim 1 is combined with one or more of an alkalizing agent, a detackifier, a pigment and a surfactant prior to being dispersed in water.

* * * * *